United States Patent
Shahar et al.

(10) Patent No.: US 7,058,441 B2
(45) Date of Patent: Jun. 6, 2006

(54) OPTICAL MEASURING SYSTEM FOR DIAGNOSING EAR CONDITIONS

(75) Inventors: Menashe Shahar, South Golan (IL); Meir Tenne, Yoqneam Village (IL)

(73) Assignee: Chameleon Medical Innovation, Ltd., Lod (IL)

( * ) Notice: Subject to any disclaimer, the term of this patent is extended or adjusted under 35 U.S.C. 154(b) by 330 days.

(21) Appl. No.: 09/987,685

(22) Filed: Nov. 15, 2001

(65) Prior Publication Data

US 2002/0087084 A1    Jul. 4, 2002

Related U.S. Application Data

(60) Provisional application No. 60/248,593, filed on Nov. 16, 2000.

(51) Int. Cl.
*A61B 5/00* (2006.01)

(52) U.S. Cl. ..................... 600/475; 600/477

(58) Field of Classification Search ........ 600/473–478, 600/549, 200; 356/300, 302, 303, 326, 448
See application file for complete search history.

(56) References Cited

U.S. PATENT DOCUMENTS

| | | | |
|---|---|---|---|
| 4,273,110 A | | 6/1981 | Groux |
| 4,793,675 A | * | 12/1988 | Handa ............................. 385/7 |
| 4,882,492 A | | 11/1989 | Schlager |
| 5,001,556 A | | 3/1991 | Nakamura et al. |
| 5,280,788 A | | 1/1994 | Janes et al. |
| RE34,599 E | * | 5/1994 | Suszynski et al. .......... 374/158 |
| 5,363,839 A | | 11/1994 | Lankford |
| 5,379,764 A | | 1/1995 | Barnes et al. |
| 5,582,168 A | | 12/1996 | Samuels et al. |
| 5,673,692 A | * | 10/1997 | Schulze et al. ............. 600/301 |
| 5,714,832 A | * | 2/1998 | Shirrod et al. .............. 310/328 |
| 5,847,832 A | | 12/1998 | Liskow et al. |
| 5,876,121 A | * | 3/1999 | Burns et al. ................. 374/161 |
| 5,919,130 A | | 7/1999 | Monroe et al. |
| 6,110,106 A | * | 8/2000 | MacKinnon et al. ........ 600/181 |
| 6,126,614 A | * | 10/2000 | Jenkins et al. .............. 600/549 |
| 6,319,199 B1 | * | 11/2001 | Sheehan et al. ............ 600/200 |

(Continued)

FOREIGN PATENT DOCUMENTS

DE        41 33 493        4/1992

(Continued)

OTHER PUBLICATIONS

K .H. Norris. *History of NIR*, Journal of Near Infrared Spectroscopy (1996), vol. 4, pp. 31-37.

(Continued)

*Primary Examiner*—Ruth S. Smith
(74) *Attorney, Agent, or Firm*—Browdy and Neimark, PLLC

(57) ABSTRACT

A system for detecting and diagnosing ear related conditions. The system includes a device capable of obtaining a spectrum of reflected light from an ear of a subject and a processing unit in connection with the device, which is capable of translating the obtained spectrum of reflected light to one or more output values related to the condition of the ear. The invention further provides a method for detecting and diagnosing ear related conditions including the steps of illuminating inside the ear; inserting a device to the ear canal capable of conveying at least one spectrum of reflected light from the ear to a processing unit; and activating the processing unit thereby translating at least one spectrum of reflected light provided at the time of activating to one or more output values related to the condition of the ear.

26 Claims, 5 Drawing Sheets

U.S. PATENT DOCUMENTS

| | | | |
|---|---|---|---|
| 6,343,227 B1 * | 1/2002 | Crowley | 600/407 |
| 6,379,920 B1 | 4/2002 | El-Sayed et al. | |
| 6,450,970 B1 * | 9/2002 | Mahler et al. | 600/549 |
| 2002/0193671 A1 * | 12/2002 | Ciurczak et al. | 600/316 |
| 2003/0171655 A1 * | 9/2003 | Newman et al. | 600/200 |

FOREIGN PATENT DOCUMENTS

| | | |
|---|---|---|
| DE | 4133493 | 4/1992 |
| EP | 0 043 133 | 1/1982 |
| WO | WO 99/66830 | 12/1999 |
| WO | WO 00/74556 | 12/2000 |
| WO | WO 02/039874 | 5/2002 |

OTHER PUBLICATIONS

Donald A Burns, Emil W. Ciuczak. *Handbook of Near Infrared Analysis* (1992), pp. 1-18.

PCT Search Report.

Doladov, M. et al, "Optical Reflection Spectrum of the Human Tympanic Membrane", *Journal of Applied Spectroscopy*, vol. 68, No. 4, Jul. 2001, pp. 708-710.

US 6,230,044, 05/2001, Afanassleva et al. (withdrawn)

* cited by examiner

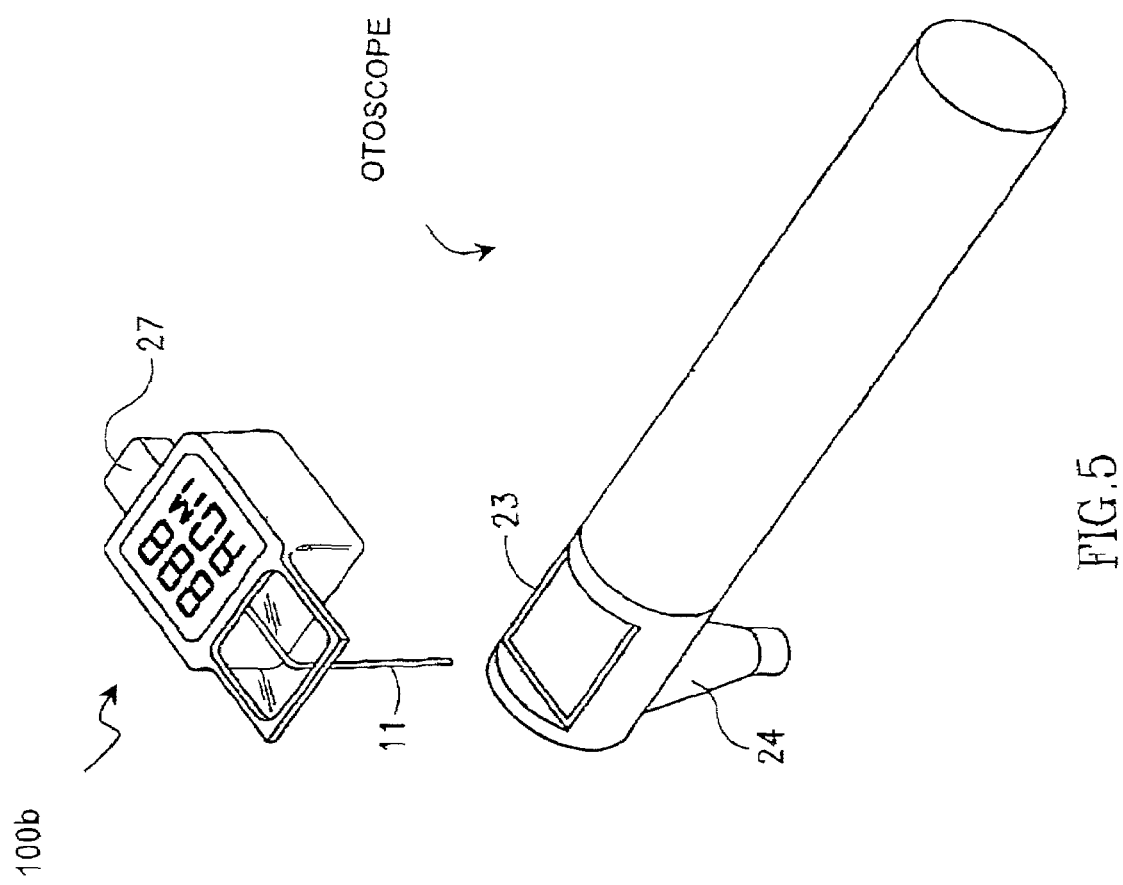

OPTICAL MEASURING SYSTEM FOR DIAGNOSING EAR CONDITIONS

This application claims the benefit of Ser. No. 60/248,593, filed Nov. 16, 2000.

FIELD OF THE INVENTION

The present invention relates generally to a diagnostic system for ear related conditions. More particularly the invention relates to a system capable of diagnosing ear conditions based on obtaining a spectrum of reflected light from an ear.

BACKGROUND OF THE INVENTION

A wide variety of diseases associated with the human ear have been identified. In children, otitis media is one of the most common pathologies. By itself, otitis media is a significant affliction, which can lead to serious long-term hearing and learning disabilities if not promptly diagnosed and treated with antibiotics. However, overdiagnosis of otitis media is problematic as well, since it causes unnecessary prescription of antibiotics, and excessive hospitalization.

Two major medical conditions are mistakably diagnosed as otitis media: the first one is a healthy ear, in which no medical therapy is of need. The second one is serous otitis media which is an allergic reaction or which is caused by a virus. Not only does serous otitis media cause the prescription of an overdose of antibiotics, it also requires a different treatment.

These ear pathologies are generally diagnosed using common diagnostic techniques, such as tympanometry or visual otoscopy.

Relating to otoscopy, it is quite clear that physicians should not rely solely on the otoscope to diagnose the medical condition of the ear. Otoscopy is largely subjective because it is a visual examination. Therefore, it usually results in overdiagnosis of otitis media.

Lately, the art of otoscopes has been contributed to by a number of systems proposing video technology. This type of otoscope is illustrated in U.S. Pat. No. 5,919,130 issued to Monroe at al. and in U.S. Pat. No. 5,363,839 issued to Lankford. Instead of viewing the ear through an eyepiece mounted on the otoscope, the physician views an image on the video monitor, but he still needs to diagnose the medical condition of the ear based on what he has viewed. Therefore, those otoscopes are limited, since they still rely on the diagnostic ability of the physician.

Since it was quite clear that physicians should not rely solely on the otoscope to diagnose otitis media, the use of confirmatory tests including tympanometry has grown. However, tympanometry may be painful and needs the cooperation of a sick child. Children with otitis media are frequently too uncomfortable to tolerate pressurization of the ear canal required by tympanometry, and are unable to be tested. In addition both tympanometry and visual otoscopy should be conducted by a highly trained physician, since it requires the interpretation of the results thereby diagnosing the medical condition of the ear. Since these techniques cannot be performed by non-medical or inexperienced personnel, efficient screening of children or infants at home or in a school is not possible with these techniques.

Therefore, there is a need for both a patient and a physician friendly instrument that enhances the ability to quickly and accurately diagnose otitis media and to clearly distinguish it from a normal ear or from an ear with serious otitis media.

SUMMARY OF THE INVENTION

One embodiment of the present invention is related to a system for detecting and diagnosing ear related conditions comprising a device capable of obtaining a spectrum of reflected light from an ear of a subject and a processing unit in connection with said device, which is capable of translating the obtained spectrum of reflected light to one or more output values related to the condition of the ear.

In one embodiment of the invention the system of the invention may be in the form of a single hand-held unit.

The system of the invention is able to determine whether the ear is healthy, or is infected with either otitis media, or serous otitis media and to further indicate the statistical confidence of its determination.

Further, in another embodiment of the invention the system is able to determine the redness degree of the tympanic membrane compared to a healthy ear.

A further embodiment of the present invention, the system is able to determine the effusion degree in the middle ear compare to a healthy ear.

According to a further embodiment of the present invention there is provided a method for detecting and diagnosing ear related conditions comprising the steps of illuminating inside the ear; inserting a device to the ear canal capable of conveying at least one spectrum of reflected light from said ear to a processing unit; and activating said processing unit thereby translating at least one spectrum of reflected light provided at the time of activating to one or more output values related to the condition of the ear.

BRIEF DESCRIPTION OF THE DRAWINGS

The present invention will be understood and appreciated more fully from the following detailed description taken in conjunction with the appended drawings in which:

FIG. 5 is a schematic illustration of a "add on" device for assembly on an existing otoscope in accordance with an embodiment of the present invention;

DETAILED DESCRIPTION OF THE INVENTION

An embodiment of a system of the present invention is a diagnostic system, which aids physicians in diagnosing ear inflammation. The system includes a device for obtaining a spectrum of light reflected from an ear and a processing unit in connection with the device for analyzing the spectrum so as to obtain information regarding the medical condition of the ear. The device comprises an illumination source for illuminating inside the ear and at least one optical fiber for conveying the reflected spectrum from the ear to the processing unit. The device is preferably in the form of an otoscope as exemplified in FIGS. 1, 2, 4 and 5. The processing unit comprises a spectral analytical instrument for receiving the reflected spectrum; and a microprocessor or a computer chip for processing the analyzed spectrum so as to obtain information regarding the medical condition of the ear.

While in one embodiment of the system and method of the present invention otitis media may be diagnosed, in alternate embodiments other diseases may be diagnosed.

In one embodiment of the present invention the spectral analytical instrument includes one or more filters which transmit specific wavelengths.

In another embodiment of the present invention as exemplified in FIGS. 1 and 3–5, the spectral analytical instrument includes a spectrometer, which, in a specific embodiment of the present invention, is sensitive to visible and near infra red radiation (e.g., wavelength of 400 nm to 1200 nm). Thus, the principles of The Near Infrared Spectroscopy, which are well known in the prior art as been described in K. H. Norris, J. Near Infrared Spectrosc. 4, 31–37 (1996) and in Handbook of Near Infrared Analysis, Donald A, Burns, Emil W. Ciuczak, (1992), P. 1–18, may be applicable herein.

The present invention will be more completely understood through the following detailed description, which should be read in conjunction with the attached drawings. All references cited herein are hereby incorporated by reference.

Figure 1:
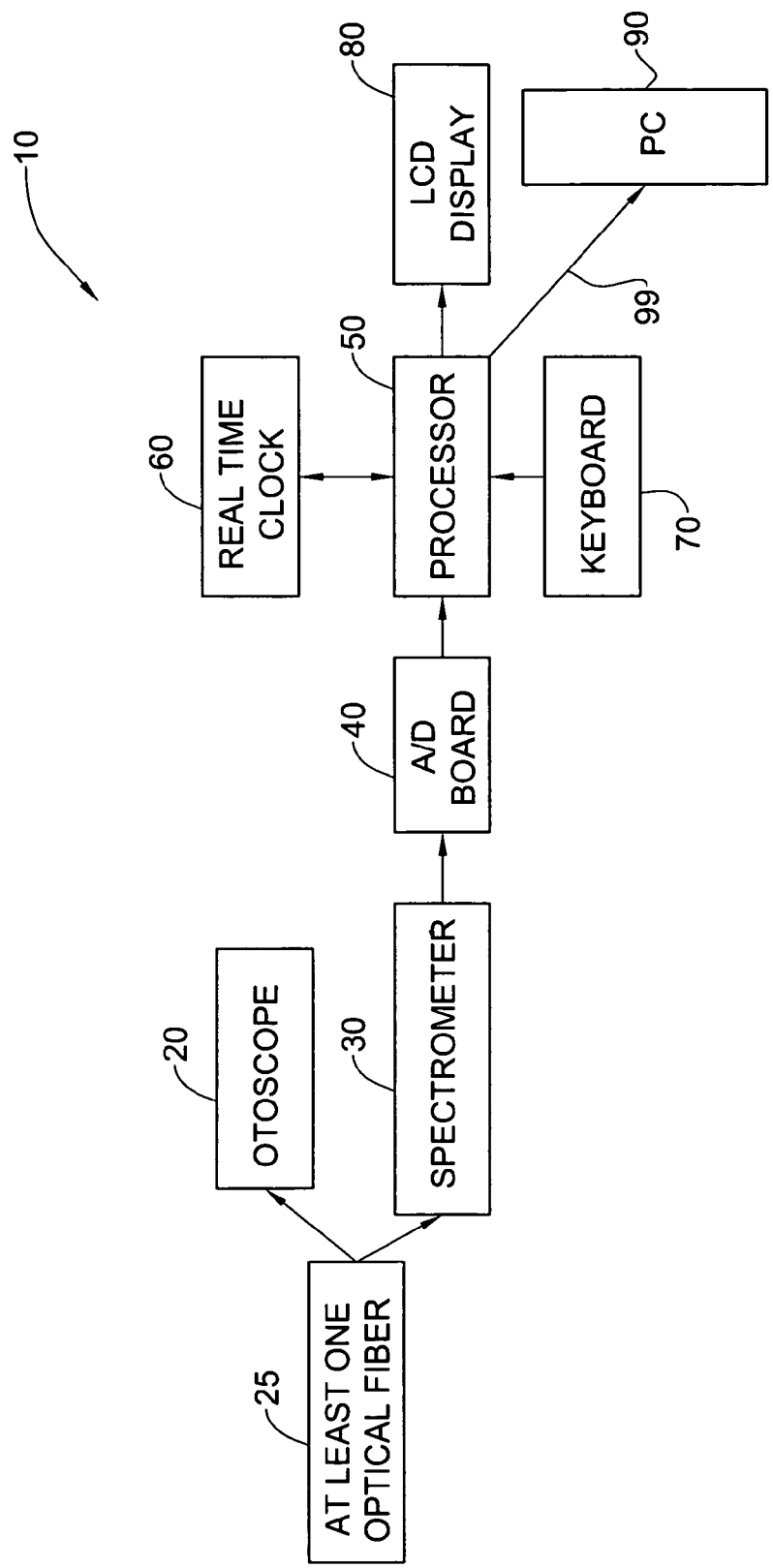
FIG. 1 is a block diagram of the system in accordance with an embodiment of the present invention.

Referring now to FIG. 1 in which a block diagram of a system 10 is shown in accordance with one embodiment of the present invention. The system 10 includes a device 20 for inserting into an ear, illuminating the ear, for example its tympanic membrane and obtaining reflected light. Device 20 may be in a form of an otoscope. Device 20 is connected to a spectrometer 30 through, for example, at least one optical fiber 25. Other methods of connecting the spectrometer to the device may be used. In an embodiment of the present invention the spectrometer is sensitive to approximately 400 nm–1200 nm wavelength. In another embodiments other wavelengths may be used. The spectrometer output may be for example a voltage or current signal that is converted to a vector of digital numbers using a 12 bit A/D converter indicated as 40. Other outputs may be used. In alternate embodiments other outputs and methods for producing an output may be used. The data is then fed to a processor 50 preferably including a memory such as an accessible memory for the actual processing. Processor 50 may be connected to, for example, a clock 60, to a keyboard 70 and to an LCD display 80. Processor 50 can further be connected to a PC indicated as 90 through a serial port indicated as 99. Other systems for processing data may be used.

Figure 2:
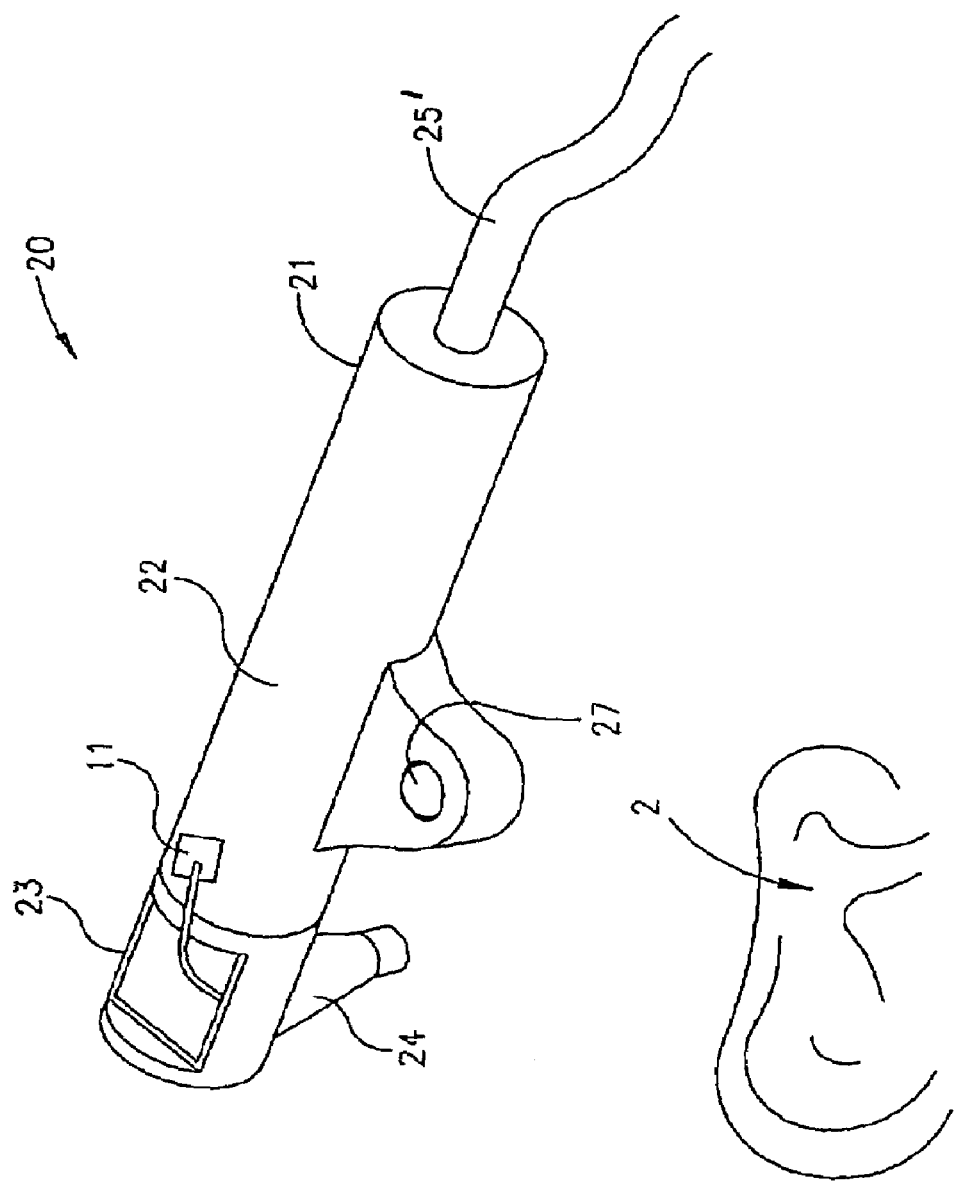
FIG. 2 is a schematic illustration of the device in a form of an otoscope according to one embodiment of the present invention.

Referring now to FIG. 2 in which a device 20 in a form of an otoscope in accordance with one embodiment of the present invention is shown. The otoscope includes an elongated housing 22 having a substantially hollow interior and proximal and distal ends 21 and 23. The distal end 23 of the elongated housing 22 is provided with a substantially frusto-conically shaped inner tip housing 24, that can also serve for illuminating inside the ear, and that can further be accompanied by a speculum—a distal extension which is sized for positioning within an ear canal 2 undergoing diagnosis for sterility purposes. The device 20 is connected to means for illuminating (not shown). As shown in FIG. 2 the means for absorbing the reflected light from the ear drum. 11 can be situated inside the hollow interior of 24. In one embodiment of the present invention the means for illuminating the ear drum is a halogen lamp, wherein the luminescence reflected on the ear drum through the inner tip housing 24. Other illuminating means may be used. In one embodiment at least one optical fiber 11 is extended from the inner tip housing 24, through the elongated housing 22 and is fanned out in the proximal end 21. An electo-optical cable 25' is further connected to spectrometer 30 (FIG. 1). On the exterior of the elongated housing 22 may be provided a freeze button 27, which is connected to the processor 50 (FIG. 1), such that when the freeze button is pressed, it activates processor 50. In one embodiment of the present invention when the freeze button 27 is pressed, processor 50 obtains and analyzes one spectrum of reflected light provided at the time of activating. In another embodiment of the present invention when the freeze button 27 is pressed, processor 50 (FIG. 1) obtains and analyzes more than one spectrum of reflected light provided at the time of activating and at a followed period of time as been predefined. A device such as a freeze button need not be used.

In one embodiment, a white patch standard reference spectrum may be acquired, before the device is used to test an ear. When not in use, the device is placed on a stand, with the optic fiber facing a standard white patch. In order to remove the device from the stand, the freeze button 27 may be pressed and by doing so, a sample of the spectrum of the white patch is acquired. This spectrum is then used as a reference spectrum for calculating the relative reflectance spectrum of the ear. Other methods may be used to calibrate the device.

Figure 3:
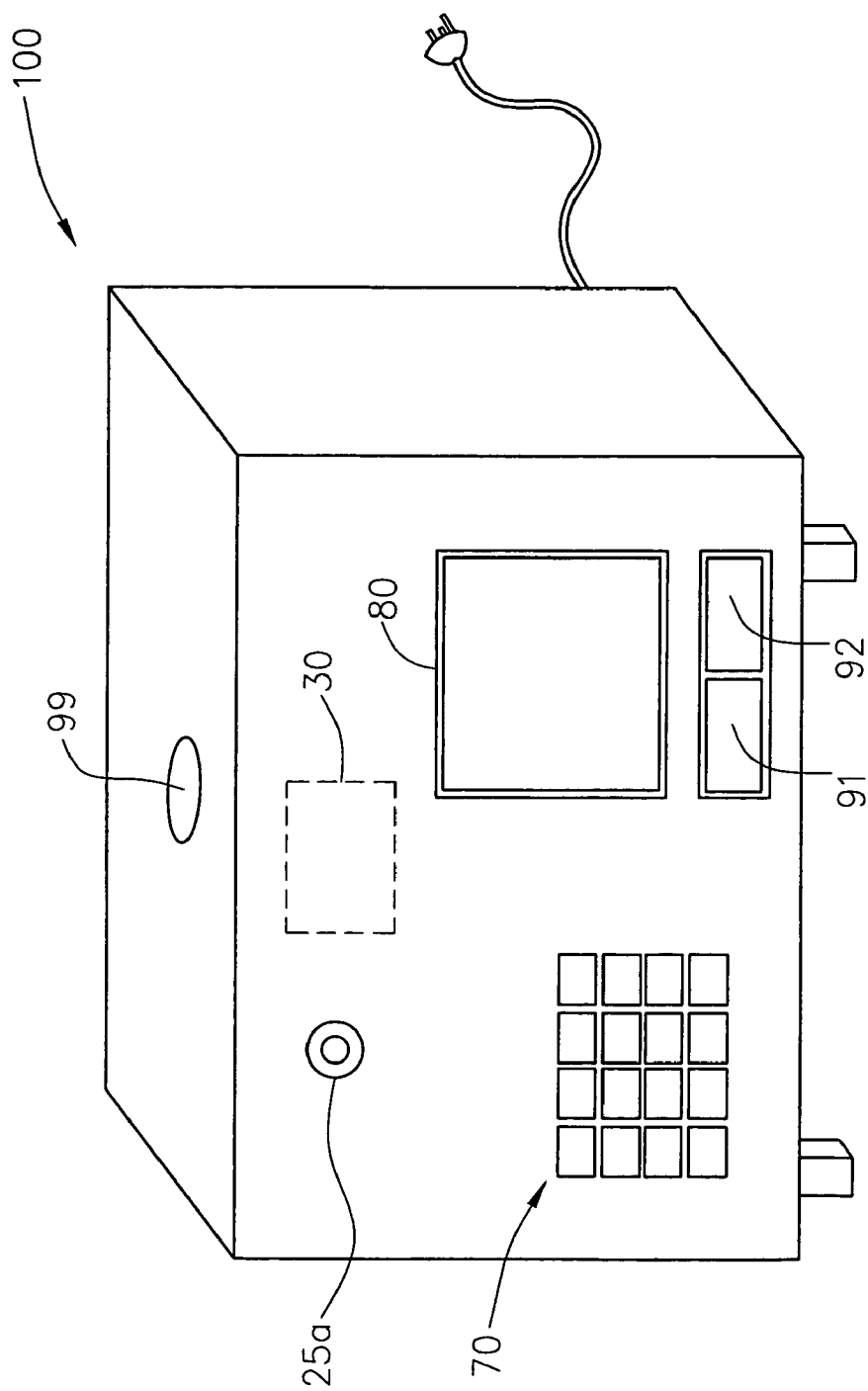
FIG. 3 is a schematic illustration of the processing unit of the present invention according to one embodiment of the present invention.

Referring now to FIG. 3 in which a processing unit 100 is shown. In front of processing unit 100 there is an LCD panel indicated as 80 and a keyboard indicated as 70 having a set of keys, for example, twelve to sixteen keys for entering patient I/D and other data. Inside processing unit 100 there is a spectrometer 30 (FIG. 1), which is connected to, for example, one electro-optical cable 25' through a connector 25a on the exterior of the processing unit 100. In another embodiment other methods of analyzing light may be used. In yet, another embodiment other data entry devices may be used.

In one embodiment, spectrometer 30 receives the reflected light from the ear, and produces an electrical signal. The spectrometer is provided with a linear photodiode array and a diffraction grating. The electro-optical cable 25' delivers the light to an entrance slit of the spectrometer. Inside the spectrometer there is a linear array having 256, 512, 1024 or 2048 photoelements, each representing a different spectral channel. Other numbers of photo elements may be used. In one embodiment the output of the spectrometer is an electrical signal (in a form of a video signal), which carries information about the light intensity in each spectral channel.

In an exemplary embodiment, inside processing unit 100 there is further provided an A/D converter indicated as 40, which converts the electrical signal to at least one digital value. The digital value is then obtained by a processor 50, which analyzes the information and saves it. Processor 50 may be further connected to a clock 60, which provides it with the time and date of the diagnosis.

In one embodiment, the LCD 80 is an alphanumeric display with 32 characters organized in two rows of 16 characters. Below the display there are two soft keys 91 and 92, the bottom line of the display may display the function of each soft key. When the system is powered on, it displays the current time on the upper line provided by clock 60. The soft keys are start and set. Pressing the start key will put the system in measurement state where it waits for the doctor to press the freeze button 27 on the device to make the actual measurement. When the freeze button is pressed the data is saved and processed. After processing is complete, the result is displayed on the top line. LCD 80 displays the result, which may be either "normal" or "serous otitis media" or "otitis media" or "undiagnosable". The result is provided with the statistical significance of the classification decision. In other embodiments, other displays and data entry systems may be used, and other diagnosis may be produced.

When result is displayed the doctor has the option to save the data by pressing the soft key. When saving the data the doctor is asked to enter the patient ID on the numeric keyboard 70, and press the left soft key for the ear side.

In one embodiment the data may be saved at the first free location found inside processor 50. Data is saved in files, each file includes a patient ID, ear side, current date and time provided by clock 60 and actual spectrometer data (two bytes per point). If more then one file was saved for the same patient on the same ear, a serial number will be appended to the name.

Figure 4:
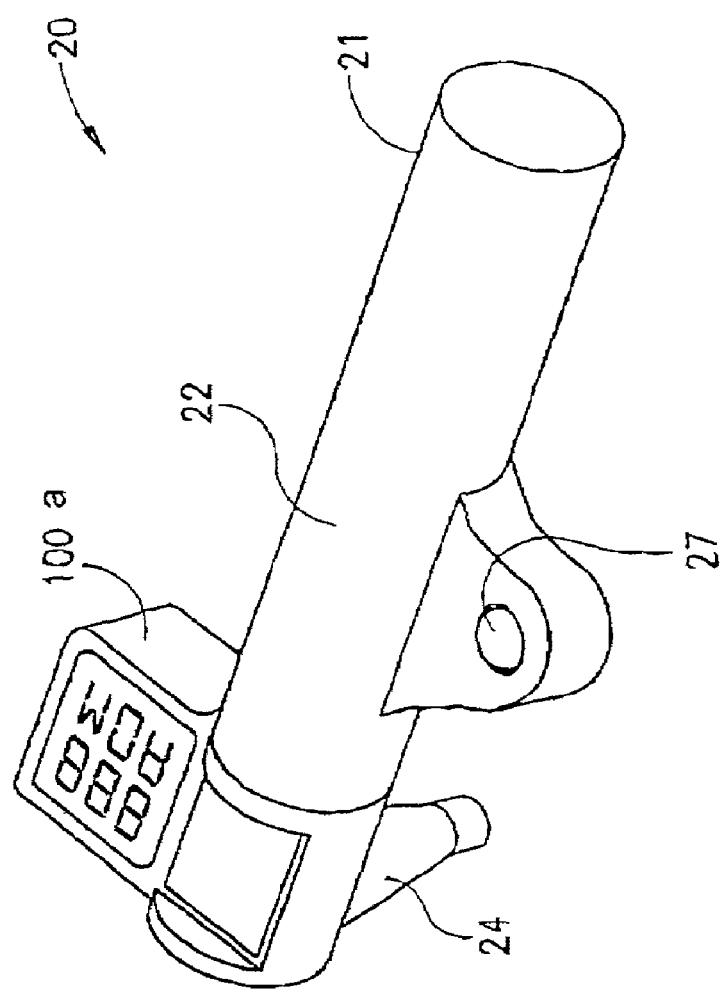
FIG. 4 is a schematic illustration of a single hand held unit in a form of an otoscope in accordance with one embodiment of the present invention.

In one embodiment of the present invention the processing unit 100 is miniaturized to be used as a single hand held unit 100a, built in with an otoscope as shown in FIG. 4.

In another embodiment of the invention, a miniaturized processing unit 100b is a separate device that can be added to any otoscope on the market, as shown in FIG. 5.

In one embodiment, the doctor can transfer a file to a PC indicated as 90 connected to the processor through, for example, a serial port 99 provided on the exterior of the processing unit. In other embodiments, other data connectors may be used. The doctor can further delete the file. The doctor has the option to delete the file after its transfer is completed. The doctor can get a list of all files stored in system memory and decide which file to transfer or delete. This entire interface is done through the keyboard 70.

Processing unit 100 can further be connected to the internet through a modem either built in the processing unit 100 or externally connected to the processing unit.

The Processing

As explained above, in one embodiment the A/D converter, indicated as 40, converts the electrical signal to at least one digital value, which is further received by a processor 50. Preferably, every digital value represents a point on the spectrum. Therefore, the number of digital values received by a processor equals the number of the photoelements of the linear array of the spectrometer. At least one digital value could be referred to as the spectrum vector. In one embodiment of the present invention, the linear array of the spectrometer consists of 2048 photoelements, thus, 2048 digital values are received by the processor 50. Each value is a 12-bit integer.

Preferably, three processes are done on the vector:

1) Smoothing and derivative
2) Model evaluation
3) Comparison of specific digital values of specific wavelength to corresponding reference values.

In other embodiments other processes may take place.

Smoothing and Derivative

In one embodiment, the operation performed on the at least one digital value is differentiation (first or higher order derivative) with smoothing in a local window (n points). The algorithm for smoothing and calculating the derivative can be simplified to a linear combination as follows:

$$D_i = \text{Sigma}(C_j * S_{i-j})_{j=-n/2}^{j=n/2}$$

Wherein:

$D_i$—Smoothed derivative value at point i;
i—Index of point;
$C_j$—Smoothing and differentiation coefficients;
S—Value of spectrum point;
n—window width for smoothing and differentiation operation.

The coefficients $C_j$ are calculated off-line using smoothing and differentiation algorithms and the calculated values are input to the processor 50 by a qualified technician. There may be a different set of coefficients for the first points and for the last points in the vector. The above equation is evaluated for every digital value. The result is a new vector of the derivative. Calculations are done in a floating point math. In alternate embodiments, smoothing and differentiation may be performed using different methods.

Model Evaluation

In one embodiment, the processed vector, $D_i$, is used as an input to a classification model that classifies the state of the inspected ear to one of three classes: (1) Normal, (2) serous otitis media and (3) otitis media. In alternate embodiments, other diagnosis may be made. The model requires at least one reference value to be input into the processing unit. In one embodiment of the present invention the technician inputs to the processor three ranges of statistical values: 1) for normal ear; 2) for ear infected with serous otitis media; 3) and for ear infected with otitis media. These statistical values are saved in the accessible memory of the processor. In addition to classifying the inspected ear, the model also provides the statistical significance (confidence level) at which the class was determined.

In another embodiment of the present invention the technician inputs to the processor at least one digital value results from diagnosing the other ear of said patient with the system of the present invention. Thus, at least one digital value of the other ear can provide at least one reference value for diagnosing the inspected ear.

In a further embodiment of the present invention the technician inputs to the processor at least one digital value resulting from a former diagnosis of the inspected ear with the system of the present invention while the inspected ear was healthy. Thus, at least one digital value resulting from a former diagnosis can provide at least one reference value for diagnosing the same ear in a later diagnosis.

Linear discriminant models can be formulated as a linear combination of the derivative vector with a set of multiplying coefficients. The coefficients are calculated using statistical optimization techniques like Regression Analysis. The confidence level of the class determination of each vector is also computed. Therefore, the output of the model consists of two numbers: one represents the class that the ear under evaluation belongs to, and the second represents the statistical significance of the classification decision.

In a case where the statistical significance of the classification decision is low, the output to the LCD display 80 is 'undiagnosed'.

Different classification models can be implemented to mathematically manipulate the processed vector $D_i$. For example, neural network classifiers, non parametric classifiers (e.g. K Nearset Neighbors) etc. All models yield the same output: classification to (1) normal, (2) serous otitis media or (3) otitis media and statistical significance (confidence level) at which the class was determined.

Comparison of Specific Digital Values of Specific Wavelength to Corresponding Reference Values.

In addition to the output regarding the classification and the statistical significance, specific information can further be provided regarding the degree of redness of the tympanic membrane and the degree of effusion (fluid) in the middle ear. This information can be provided, in one embodiment of the present invention, when at least one digital value further includes values of the reflectance at wavelengths of, for example 650–700 nm and 962 nm. As it is well known in the art 962 nm is the wavelength of reflectance of water, and 650–700 nm is the range of wavelengths of reflection of the red color in the white light spectrum. Before the processing step the technician inputs to the system at least one reference value which according to one embodiment of the present invention includes statistical values of the reflectance of a healthy ear in the wavelengths of 650–700 nm and 962 nm, and from comparing these reference values to their corresponding experimental values the output regarding the degree of redness of the tympanic membrane and the degree of effusion in the middle ear are provided.

FIG. 4 illustrates one of the embodiments of the present invention wherein the system is provided as a single hand held unit. On the exterior of device 20, as described in reference to FIG. 2, is placed processing unit 100a, which is described in reference to FIG. 3, and that was further miniaturized in order to be used as a hand held unit.

FIG. 5 illustrates another embodiment of the present invention wherein the system is provided as a single hand held unit, and wherein processing unit 100a, which is described in reference to FIG. 3, was further miniaturized, and was placed on any otoscope that is available on the market.

Experimental Evaluation

In order to demonstrate the diagnostic properties of the system of the present invention a diagnostic study was carried out in 258 volunteers males and females. Custom software was written for system and user interface, as well as data analysis and data management. Each acquired sample was labeled by an expert doctor as NORMAL, ACUTE OTITIS MEDIA (AOM) or SEROUS OTITIS MEDIA (SOM), using a microscope otoscope. The work included 258 patients, out of which 511 samples were usable and were analyzed.

Data analysis was performed in two stages: (1) A statistical model was built from part of the data set (training/calibration)and (2) The constructed model was used to predict the rest of the samples of the data (testing/validation)

In order to obtain robust results, the above procedure was performed several times and the average performance is reported in what follows (cross validation of the model by venetian blinds).

The performance of the models was evaluated by four parameters:
1. Percentage of AOM cases (out of all AOM cases) that were correctly predicted.
2. Percentage of AOM cases (out of all AOM cases) that were not correctly predicted (false negative)
3. Percentage of NORMAL cases (out of all NORMAL cases) that were erroneously predicted as AOM (false positive (N)).
4. Percentage of SOM cases (out of all SOM cases) that were erroneously predicted as AOM (false positive (S)).

The analysis was performed on the whole data base, as well as on a subset of the data base that included only patients under 12 years old.

Table 1 summarizes the results by depicting the performance factors, as defined above:

TABLE 1

| | Performance factors in cross validation | | | |
|---|---|---|---|---|
| Age group | AOM Accuracy | AOM false negative | NORMAL false positive (N) | SOM false positive (S) |
| All | 89% | 11% | 1% | 9% |
| Under 12 | 93% | 7% | 2% | 11% |

It will be appreciated that the present invention is not limited by what has been described hereinabove and that numerous modifications all of which fall within the scope of the present invention, exist. For example, certain assumptions were necessarily used in computing the mathematical models of the embodiments. Values and equations based on these assumptions can be changed if new information becomes available.

It will be appreciated by persons skilled in the art that the present invention is not limited by what has been particularly shown and described herein above. Rather the scope of the invention is defined by the claims which follow:

The invention claimed is:

1. A system for use in detecting and diagnosing ear related conditions, the system comprising:
   (a) a device capable of obtaining a spectrum of reflected light from an ear of a subject; and
   (b) a processing unit in connection with said device which is capable of translating the obtained spectrum of reflected light to one or more output values related to the condition of the ear, the processing unit comprising a spectral analytical instrument in the form of a spectrometer, which receives said spectrum of reflected light and produces an analog signal indicative thereof, the processing unit being preprogrammed with certain models capable of analyzing the analog signal and converting it to at least one digital value presenting a spectrum vector indicative of a determined state of the ear, processing the spectrum vector by comparing to at least one predetermined reference value, and applying a classification model to the processed spectrum vector to thereby classify the determined state of the ear and generate output data indicative of one of the following ear conditions: normal condition, serous otitis media condition, and otitis media condition.

2. The system of claim 1, wherein said spectrometer is sensitive to wavelengths of approximately between 400 nm to 1200 nm.

3. The system of claim 1, wherein said spectral analytical, instrument includes at least one filter.

4. The system of claim 1, wherein said processing unit further comprises a microprocessor interfaced with said converter.

5. The system of claim 4, wherein said microprocessor comprises an accessible memory.

6. The system of claim 1, wherein said processing unit comprises a display for displaying said one or more output values.

7. The system of claim 6, wherein said display includes an LCD display.

8. The system of claim 1, wherein said one or more output values indicate the health of the ear.

9. The system of claim 8, wherein said one or more output values indicate whether there is otitis media or serous otitis media.

10. The system of claim 9, wherein the statistical confidence of a decision relating to the existence of otitis media or serous otitis media is additionally indicated.

11. The system of claim 1, wherein said at least one reference value is at least one digital value resulting from diagnosing the other ear of said subject with said system.

12. The system of claim 1, wherein said at least one reference value is at least one digital value resulting from a diagnosis of a healthy ear with said system.

13. The system of claim 1, wherein said at least one reference value is a statistical range of values resulting from healthy ears.

14. The system of claim 1, wherein said at least one reference value is a statistical range of values resulting from ears with otitis media.

15. The system of claim 1, wherein said at least one reference value is a statistical range of values resulting from ears with serous otitis media.

16. The system of claim 1, wherein said processing unit further comprises an input unit including at least a numeric keyboard and an LCD display, for inputting information, and for further saving said information with said one or more output values in a file.

17. The system of claim 16, wherein said information includes at least one of the following: user data and the side of said ear.

18. The system of claim 16, wherein said processing unit further comprises a clock for indicating the time and date of said one or more output values, and wherein the processing unit further saves said time and date with said one or more output values in said file.

19. The system of claim 16, wherein said processing unit is in communication with a personal computer.

20. The system of claim 1, wherein said system is incorporated into a single hand-held unit.

21. The system of claim 20, wherein the single hand-held unit is an otoscope.

22. The system of claim 1, wherein said device capable of obtaining a spectrum of reflected light is incorporated into an otoscope.

23. The system of claim 1, wherein the processing unit is configured to be connected to the internet.

24. The system of claim 1, wherein said processing unit is operable to translate at least one selected region of the obtained spectrum of the reflected light to said one or more output values related to the condition of the ear.

25. A system for use in detecting and diagnosing ear related conditions, the system comprising:
(a) a device capable of obtaining a spectrum of reflected light from an ear of a subject; and
(b) a processing unit in connection with said device which is capable of translating the obtained spectrum of reflected light to one or more output values related to the condition of the ear, the processing unit comprises a spectral analytical instrument in the form of a spectrometer for receiving said spectrum and producing an analog signal indicative thereof, the processing unit being preprogrammed with certain models capable of analyzing the analog signal and converting it to at least one digital value presenting a spectrum vector indicative of a determined state of the ear, processing the spectrum vector by comparing it to at least one predetermined reference value, and applying a classification model to the processed spectrum vector thereby classify the determined state of the ear and generate output data indicative of one of the following ear related conditions: normal condition, serous otitis media condition, and otitis media condition, wherein said at least one digital value includes at least one digital value of a reflectance at wavelength of approximately 650–700 nm, the processing unit being configured and operable for further comparing said value to a statistical reflectance at wavelength of approximately 650–700 nm of a healthy ear thereby determining the redness degree of the tympanic membrane of said ear.

26. A system for use in detecting and diagnosing ear related conditions, the system comprising:
(a) a device capable of obtaining a spectrum of reflected light from an ear of a subject; and
(b) a processing unit in connection with said device which is capable of translating the obtained spectrum of reflected light to one or more output values related to the condition of the ear, the processing unit comprises a spectral analytical instrument in the form of a spectrometer for receiving said spectrum and producing an analog signal indicative thereof, the processing unit being preprogrammed with certain models capable of analyzing the analog signal and converting it to at least one digital value presenting a spectrum vector indicative of a determined state of the ear, processing the spectrum vector by comparing it to at least one predetermined reference value, and applying a classification model to the processed spectrum vector to thereby classify the determined state of the ear and generate output data indicative of one of the following ear related conditions: normal condition, serous otitis media condition, and otitis media condition, wherein said at least one digital value includes a digital value of a reflectance of wavelength of approximately 962 nm, the processing unit being configured and operable for further comparing said value to a statistical reflectance at wavelength of approximately 962 nm of a healthy ear thereby determining the effusion degree in the middle ear.

* * * * *

UNITED STATES PATENT AND TRADEMARK OFFICE
CERTIFICATE OF CORRECTION

PATENT NO. : 7,058,441 B2  
APPLICATION NO. : 09/987685  
DATED : June 6, 2006  
INVENTOR(S) : Shahar et al.

It is certified that error appears in the above-identified patent and that said Letters Patent is hereby corrected as shown below:

On the cover, section 75, in the list of inventors delete "Meir Tenne, Yoqneam Village (IL)" and insert -- Victor Alchanatis (IL) ; Ze' ev Schmilovitch (IL) --.

Signed and Sealed this

Twenty-ninth Day of January, 2008

JON W. DUDAS  
*Director of the United States Patent and Trademark Office*